United States Patent

Lilge et al.

Patent Number: 5,275,160
Date of Patent: Jan. 4, 1994

[54] PROBES FOR RADIANCE DOSIMETRY

[75] Inventors: Lothar Lilge, Frankfurt am Main, Fed. Rep. of Germany; Brian C. Wilson, Toronto, Canada; Thomas Haw, Boston, Mass.

[73] Assignee: The General Hospital Corporation, Boston, Mass.

[21] Appl. No.: 641,152

[22] Filed: Jan. 14, 1991

[51] Int. Cl.⁵ .............................................. A61B 5/00
[52] U.S. Cl. .................................. 128/634; 128/633; 128/665; 422/82.08
[58] Field of Search ............... 128/633, 634, 664, 665, 128/666; 422/82.05, 82.08, 82.09; 356/436

[56] References Cited

U.S. PATENT DOCUMENTS

| | | | |
|---|---|---|---|
| 4,200,110 | 4/1980 | Peterson et al. | 128/634 |
| 4,861,520 | 8/1989 | van't Hooft et al. | 128/659 |
| 4,892,383 | 1/1990 | Klainer et al. | 128/634 |
| 4,999,306 | 3/1991 | Yafuso et al. | 128/634 |
| 5,000,901 | 3/1991 | Iyer et al. | 128/634 |
| 5,037,615 | 8/1991 | Kane | 128/634 |
| 5,039,492 | 8/1991 | Saaski et al. | 128/633 |
| 5,173,432 | 12/1992 | Lefkowitz et al. | 128/633 |

OTHER PUBLICATIONS

Wilson et al., Photochem. Photobiol., 47:153, 1975.
Marijnissen et al., Laser Med. Surg., 7:235, 1987.
Star et al., Photochem. Photobiol. 46:619, 1987.
Star et al., Appl. Optics, 28:2281, 1989.
Ishimaru, Appl. Optics, 28:12 (1989).
Svaasand et al., Appl. Optics. 28:12 (1989).
Bolin et al., Photochem. Photobiol. 46:5, pp. 609–617 (1987).
Jacques, Appl. Optics. 28:12 (1989).
Yoon et al., Appl. Optics. 28:12 (1989).
Flock et al., IEEE Biomed. Eng. 36:12 (1989).

Primary Examiner—Lee S. Cohen
Assistant Examiner—Brian L. Casler
Attorney, Agent, or Firm—Fish & Richardson

[57] ABSTRACT

The invention features a probe for radiance dosimetry. The probe includes a tip portion containing a fluorescent dye connected to a translucent spacer element.

9 Claims, 11 Drawing Sheets

FIG. 1 
— NBA IN MeOH 1:3 DILUTED
— NBA FREE BASE IN MMA

PROBES FOR RADIANCE DOSIMETRY

This invention was made with Government support under Contract #N00014-86-K-0017 awarded by the Office of Naval Research. The Government has certain rights in this invention.

BACKGROUND OF THE INVENTION

This invention was made in the course of work supported by the United States Government, which has certain rights in the invention.

The field of the invention is probes for radiance dosimetry.

The spatial distribution of radiance in tissue is of fundamental importance in many applications of photobiology and laser medicine. For example, in photodynamic therapy of solid tumors, irradiation of the tissue with energy of appropriate wavelength following administration of a photosensitizing dye leads to tumor destruction. The efficacy and safety of this treatment depends, among other factors, on delivering an adequate radiant energy fluence (J/cm$^2$) throughout the target tumor tissue, while sparing as far as possible the adjacent normal tissue.

There are two general approaches to determining radiant energy fluence distributions in tissue: (1) to measure the optical absorption and scattering properties of the tissue at the wavelength of interest and then to use these data to calculate the spatial distribution of fluence or absorbed energy using an approximate analytic or numerical model of light transport such as diffusion theory (Doiron et al., in *Porphyrin Photosensitization;* Kessel et al., eds. pp. 63-76, Plenun, N.Y., 1983; Ishimau et al., *Appl. Opt.* 28:2210, 1989; Flock et al., *IEEE Trans. Biomed. Eng.*, 1986) or Monte Carlo simulation (Flock et al., supra; Jaques et al., *Appl. Opt.* 28:2223, 1989); and (2) to measure directly the fluence rate at the point of interest within the tissue during irradiation. The first, indirect method has the advantage that it may be possible to determine the average tissue optical properties, and hence the fluence distribution, at all points non-invasively, for example by diffuse reflectance spectroscopy. The accuracy of this method is likely to be limited in the case of small tissue volumes of complex shape or if the tissue is optically heterogeneous on a scale comparable to the distances over which changes in radiance fluence are significant (Yoon et al. *Applied Optics* 28:2250, 1989).

The second, direct method is necessarily invasive and only a limited number of localized measurements can be made. In addition, a major challenge has been to make interstitial probes which have an isotropic response. For example, using a cut-end optical fiber connected to a photodetector, only radiance within a restricted solid angle determined by the numerical aperture is collected. The signal measured at a given orientation then depends on the radiance pattern at the specific location in the tissue. Hence, unless the radiance field is isotropic at this location, it is necessary to integrate the measurements from several directions. This has been done in vivo (Doiron et al., supra; Wilson et al., *Photochem. Photobiol.* 47:153, 1975) and has the advantage that very small diameter fibers may be used which can be placed in tissue easily and relatively non-traumatically, but this may not be a generally applicable technique. In order to measure the true fluence by a single measurement even in an anisotropic field, optical fiber probes have been developed with a spherical tip which is highly light scattering (Star et al., *Photochem. Photobiol.* 46:619, 1987; Marijnissen et al., *Laser Med. Surg.* 7:235, 1987; Star et al., *Appl. Opt.* 28:2281, 1989; Marijnissen et al., in *Photodynamic Therapy of Tumors and of Diseases,* Jori et al., eds., pp. 387-380, Libreria Progetto, Padua, 1985). Such probes have an approximately isotropic response, between the forward direction and about 150°, the backward direction having low response because of shielding where the fibers are attached to the tip. Within this angular range, isotropy of about ±10% has been achieved with 800 μm diameter tips on a 400 μm core fiber. The scattering tip of this type of probe must be large enough to make the response isotropic. Further, scattering ball tips are often quite fragile, and this characteristic makes it difficult to use them safely and easily in many solid tissues. They have been widely used for studies in liquids or gel tissue-simulating phantoms and for monitoring within body cavities such as the bladder (Star et al., *Photochem. Photobiol.* 46:619, 1987; Marijnissen et al., in *Photodynamic Therapy of Tumors and of Diseases,* Jori et al., eds., Libreria Progetto, Padua, 1985).

SUMMARY OF THE INVENTION

In general the invention features a probe for radiance dosimetry. The probe includes a tip portion connected to a translucent spacer element, and the tip portion includes a fluorescent dye. In a preferred embodiment the probe includes polymethylmethacrylate. In preferred embodiments the fluorescent dye is Nile Blue A; is Rhodamine 610; is Coumarine 440. In a preferred embodiment the spacer element is attached to an optical fiber. In a preferred embodiment the probe has a diameter of less than 1 mm.

In another aspect the invention features an instrument for radiance dosimetry, the instrument includes a probe of the invention, the spacer element of the probe being attached to an optical fiber which is in turn operably attached to a photodiode.

The probe of the invention has a small diameter for mechanical strength and ease of insertion into tissue (thus minimizing tissue damage), while providing good isotropic response.

Other features and advantages of the invention will be apparent from the following description of the preferred embodiments thereof, and from the claims.

DETAILED DESCRIPTION

Fluorescent Fiber Probes

Probes of the invention for the measurement of energy fluence in tissues are sensitive for low levels of irradiance (e.g., <200 mW/cm$^2$), and both linear and isotropic in their response. These qualities are incorporated into a device which is mechanically strong and which can be inserted without undue tissue damage.

The probes described below employ a tip containing a fluorescent dye joined to an optical fiber. The tip itself can be made of optical fiber material. The fluorescent tip absorbs radiance at one wavelength and re-emits at a different wavelength; the emitted radiance is detected at the end of an optical fiber attached to the tip. The emitted radiance, which is detected and quantified by any appropriate means, serves as a measure of the absorbed radiance. The fluorescent tip is joined to the optical fiber through a spacer element. The spacer element is translucent; this allows the tip to detect radiance coming from nearly behind the probe, radiance that would otherwise be blocked by the optical fiber.

The tip and the spacer element are made from materials which are translucent to the radiance to be detected. The fluorescent dye must be able to dissolve (or at least become suspended) in the material used to form the tip. Generally, materials used to form optical fibers are of the type which can be used to form the tip and the spacer element.

The fluorescent dye is chosen to absorb radiant energy of the wave length which is to be measured and to reemit radiance of a wavelength which can be detected. Dyes with greater quantum yields are preferred because they provide greater sensitivity.

While there is considerable flexibility in the choice of fluorescent dye and the materials used to form the probe, certain principles should be taken into account in designing the probe and joining it to the detector.

The sensitivity of these probes depends on the volume and geometry of the tip, the spacer element, and the optical fiber. The sensitivity, S/F (where S/F=W measured the photodetector)/(w/cm$^2$ incident fluence rate)) can be approximated using the following equation:

$$S/F = \alpha \Phi A H c \mu$$

α is the fraction of the incident fluence passing the tip, which is absorbed by the dye. The value of can be determined empirically and depends on dye type and volume. Obviously, larger values of α lead to greater sensitivity; however, if α is too large, the detector will interfere with the local fluence. Preferred values of α are no greater than 0.1. Φ is the fluorescence quantum yield of the dye. The value of Φ is known for some dyes; however, the value depends on the environment of the dye, e.g., the substance in which it is suspended. A is the cross-sectional area of the fluorescent tip. H is the solid angle obtained by the equivalent point source at the optical fiber input face, i.e., at the junction between the spacer element and the optical fiber. Shortening the spacer element increases H and thus increases sensitivity. However, a shorter spacer element will increase the shadowing effect of the optical fiber on the fluorescent tip. C is the coupling efficiency of the junction between the spacer element and the fiber optic bundle. μ is the transmission of the spectral filters (see below) and optical fibers interposed between the tip and the detector as integrated over the fluorescence emission spectrum. This calculation does not take into account internal reflection of excitation and emitted radiance (see below), nor the limited numerical aperture of the fiber (bundle) which also limits the efficiency of the coupling. The self-absorption of the fluorescent radiance is also ignored, since this is very small. The theoretical sensitivity for various diameters, size, and dye concentrations is given in Table 1. For the calculations in Table 1, the fluorescence is assumed to be created by a point source positioned at the center of the dyed part of the probe. If the point source were positioned at the top of the probe, the sensitivity S/F would be reduced by 0.72. Experimental values for a 3 mm diameter fluorescent fiber probe and a 1.4 mm diameter fluorescent fiber probe are also given in Table 1. These probes were constructed and tested as outlined below. In these examples, the probe with the smaller diameter was made with a higher dye concentration in the tip so that the same fractional absorption of the incident radiance beam ($\alpha$) was observed for both probes. The relatively good agreement between the theoretical and experimental values illustrate the value of the model.

TABLE 1

| Theoretical Estimated and Measure Sensitivity | | |
|---|---|---|
| Diameter (mm) | S/F(cm$^2$)-theoretical | S/F(cm$^2$)-measured |
| 3.0 | $1.8 \times 10^{-4}$ | $1.1 \times 10^{-4}$ |
| 1.4 | $4.0 \times 10^{-5}$ | $2.3 \times 10^{-5}$ | spacer element = 2.3 diameters, $\alpha = 0.1$, H = 0.031, $\Phi = 0.8$, c = 0.8, $\mu = 0.8$ Several fluorescent fiber probes and several methods for their production are described below. All of these probes have a dye containing tip portion and a dye-free spacer element portion. In use these probes are attached to an optical fiber which transmits the emitted radiance to a device capable of measuring that radiance. Any appropriate device can be employed, e.g., a photomultiplier, a photodiode, or a single photon counting device. Generally one or more filters are interposed between the optical fiber transmitting radiance from the probe and the detection device; this filter serves to block incident radiance from impinging on the detector.

Figure 17:
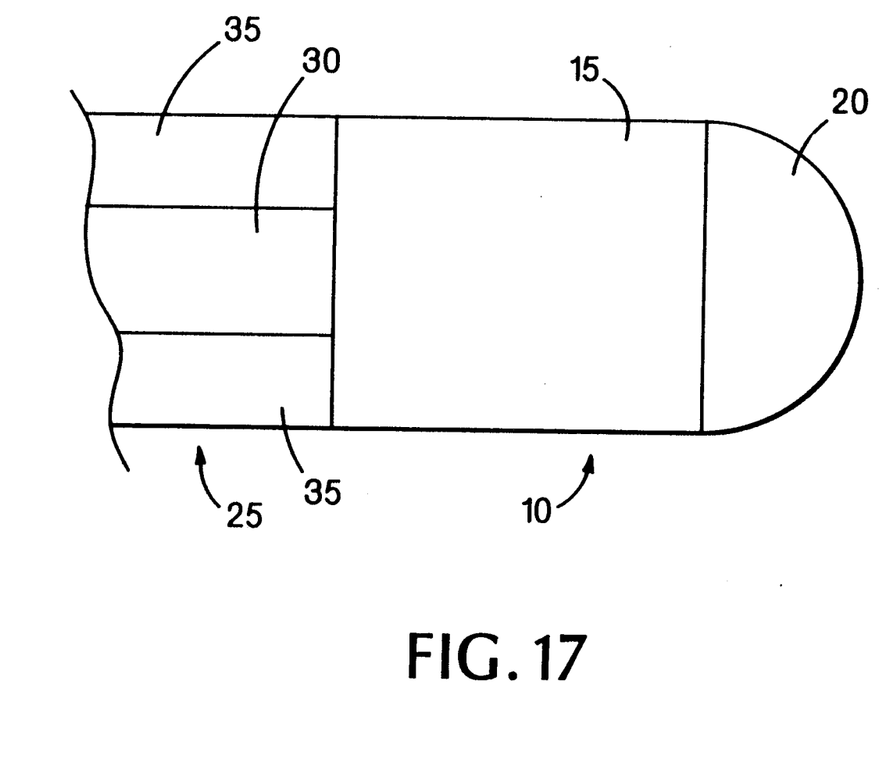
FIG. 17 is a diagram of a logitudinal section of one fluorescent fiber probe of the invention fused to an optical fiber.

A longitudinal section of preferred configuration of the fluorescent fiber probe fused to an optical fiber is illustrated in FIG. 17, in which probe 10 includes translucent spacer element 15, fused to dye-containing tip 20. The end of translucent spacer element 15, distal to dye-containing tip 20, is fused to optical fiber 25 which includes core 30 and coating 35. Preferably, the optical fiber, spacer, and probe tip have substantially the same diameter, as shown. Optical fiber 25 is operably connected to a photodiode 40, shown diagrammatically in FIG. 17.

EXAMPLE 1

Fluorescent Fiber Probes with Diameters of 3 mm and 1.4 mm

Several fluorescent fibers probes were made from polymethylmethacrylate (PMMA) doped with varying concentrations of Nile Blue in polyvinyl alcohol (PVA) as follows. Nile Blue A (0.52 mg, Aldrich, Milwaukee, Wis.) was dissolved in 0.5 ml methanol. Next 10 mg PVA (Polyscience, Warrington, Pa.) were added to create solution A. Solution B was made by combining methylmethacrylate (MMA) with Azobis (1 mg/4 ml MMA), as a polymerization initiator, and 10 mg PVA. Solution B was stirred for 15 minutes at room temperature. The dye concentration in the tip was varied by mixing solutions A and B in the appropriate ratio. After the two solutions were combined, the remaining PVA was allowed to precipitate. For polymerization, the translucent solution was poured into a 5 mm diameter hollow glass tube to a length of 10 mm, and kept 48 hours at 60° C., followed by 48 hours at 100° C. A further 15 mm long dye-free PMMA (Solution B) was added to the tube and fused in a second polymerization step to form the spacer element. After complete polymerization the probe is modeled on a lathe and polished with silica paper or a buffing compound designed for PMMA. The probe is then balanced on a 3 mm fiber optic bundle; this arrangement is solely for analysis of probe characteristics. In actual use the probe would be fused to the optical fiber bundle as described below.

1.4 mm diameter fluorescent fiber probe was constructed and attached to a 1.00 mm core quartz fiber (Superguide PSC with tefzel jacket, Fiberguide Industries, Shipley, N.J.). A 5 mm diameter fluorescent tip with the required concentration and dye-free spacer element was prepared. A 1.2 mm hole was drilled along the axis in the dye-free part to give the required spacer element where the optical fiber was inserted. The rod was then cut and machined to the required diameter and tip shape. Next the fiber was inserted and fused with Methylchloride (Sigma St. Louis, Mo).

Measurement of Linearity

Figure 1:
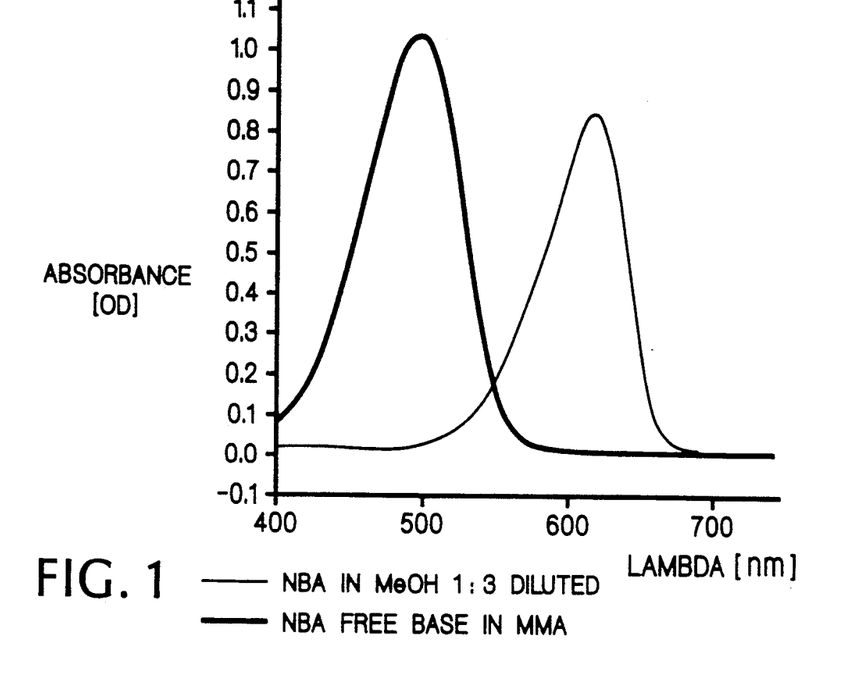
FIG. 1 is a graph which illustrates the absorbance spectra for Nile Blue A in methanol (thin line) and in methylmethacrylate (thick line).
Figure 2:
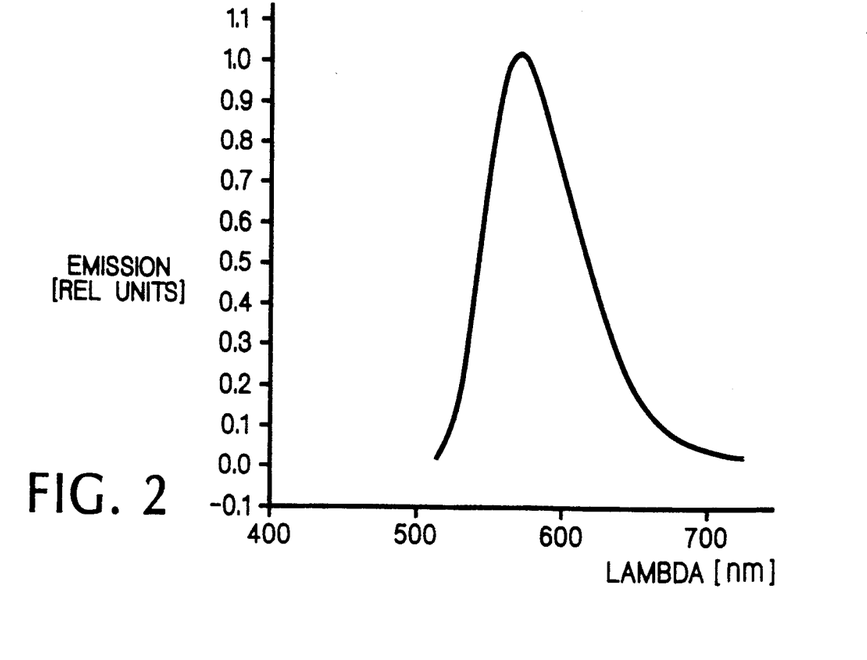
FIG. 2 is a graph which illustrates the fluorescence emission spectra of Nile Blue A in methylmethacrylate.
Figure 3:
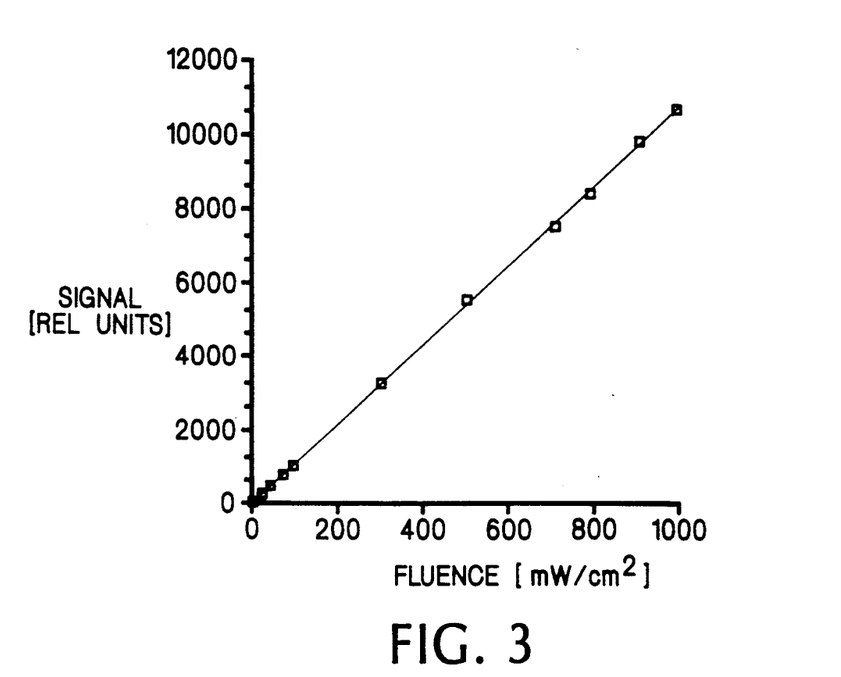
FIG. 3 is a graph which illustrates the measured signal as a function of incident radiant energy fluence rate for a 3 mm diameter fluorescent fiber probe with 10% absorption, 3 mm fluorescent tip length, and 7 mm spacer element length.

The response linearity of a 3 mm diameter probe prepared as described above was tested by varying the incident fluence rate and measuring the signal amplitude. The output of the laser was varied with neutral density filters from <1 mW/cm$^2$ to 800 mW/cm$^2$. FIG. 3 shows a typical result for this fluorescent fiber probe. At an incident fluence of 1 mW/cm$^2$ the signal to noise ratio was about 1. Noise was created by remaining unshielded room light and the pre amplifier (amplification factor 174).

The slope of such plots depends on a number of factors including on the volume of the fluorescent dye, dye concentration and coupling efficiency into the optical fiber bundle.

Measurement of Isotropy

For the isotropy measurements, 3 mm diameter fluorescent fiber probes were used. The length of the fluorescent tip and the length of the dye-free spacer element were varied between 2 and 10 mm. The terminus of the probe was either cut flat or modeled to a roughly hemispherical dome. The sides and ends of the probes were buffed to a high polish. The dye concentration was adjusted to correspond to between 1% and 10% absorption of 514 nm light over the diameter of the tip.

To measure the angular sensitivity (isotropy) of the probes, an optical fiber with telescope optics as a beam expander was moved around the fluorescent tip in an arc. The beam diameter was at least twice the length of the probe. The radiance source was an argon laser (Coherent, Palo Alto, Calif.) mechanically chopped at 30 Hz. The 3 mm diameter probe was positioned centrally on the end of a 3 mm core optical fiber bundle. To attenuate the remaining excitation radiance, a gelatin cut-on filter ($\lambda = 540$ nm, Kodak, Rochester, N.Y.) was placed between probe and fiber bundle, thus avoiding induced fluorescence in the epoxy of the fiber bundle. The fluorescence signal from the fluorescent tip was selected by a cut-on filter at 570 nm placed between the other end of the fiber bundle and a silicon photodiode (FND 100Q EG&G, Salem, Mass.). The signal was amplified and displayed on a storage oscilloscope (Le Croy, Spring Valley, N.Y.), and recorded on an IBM computer. Measurements were made at 10° intervals between 0° and 160°.

Figure 4:
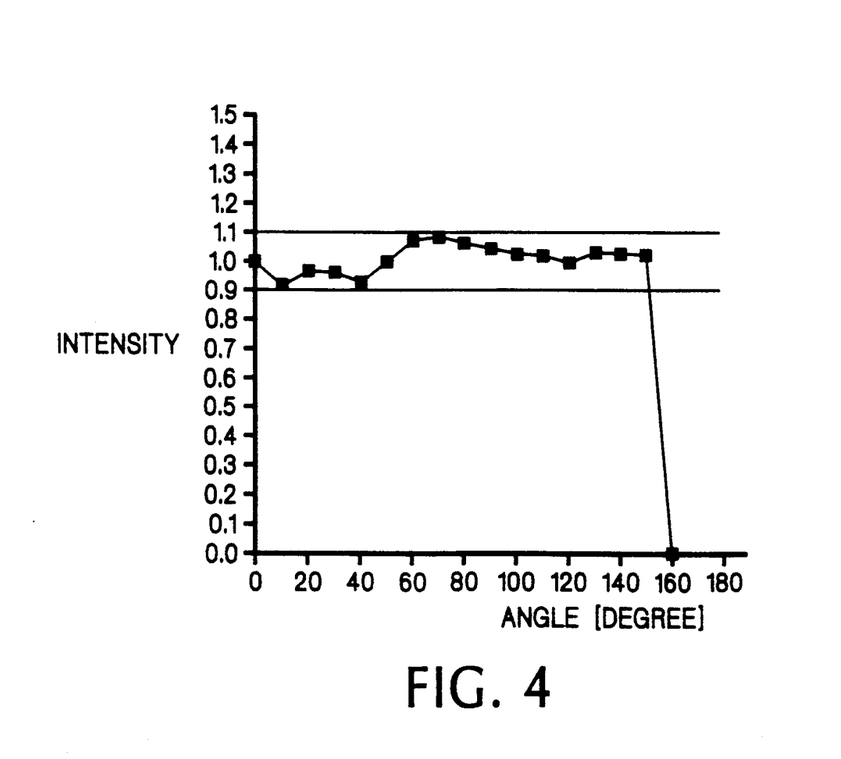
FIG. 4 is a graph which illustrates the signal intensity as a function of the angle of incident radiance for a 3 mm diameter fluorescent fiber probe with 10% absorption, 3 mm fluorescent tip length, 7 mm spacer element length and a domed proximal end.
Figure 5:
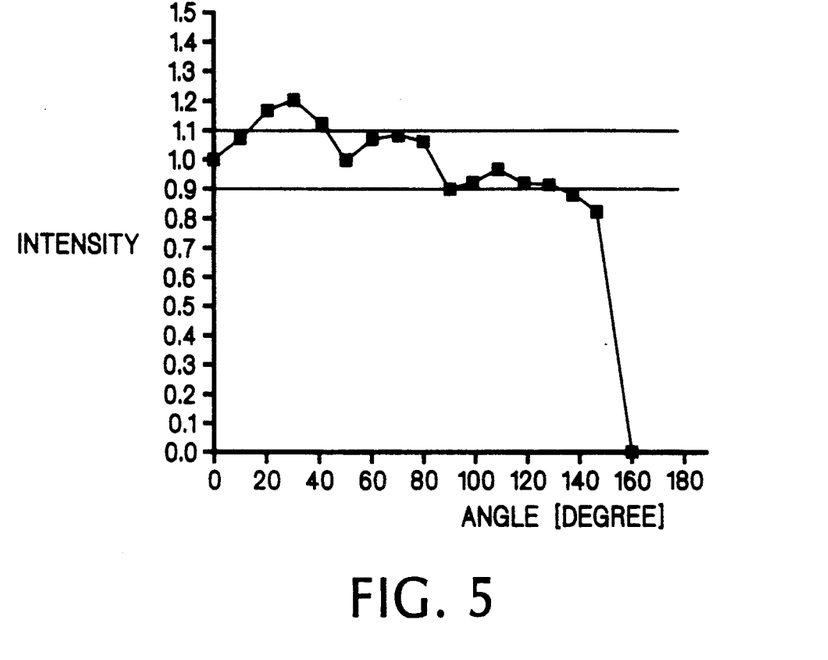
FIG. 5 is a graph which illustrates the signal intensity as a function of the angle of incident radiance for a 3 mm diameter fluorescent fiber probe with 10% absorption, 3 mm fluorescent tip length, 7 mm spacer element length, and a flat proximal end.
Figure 6:
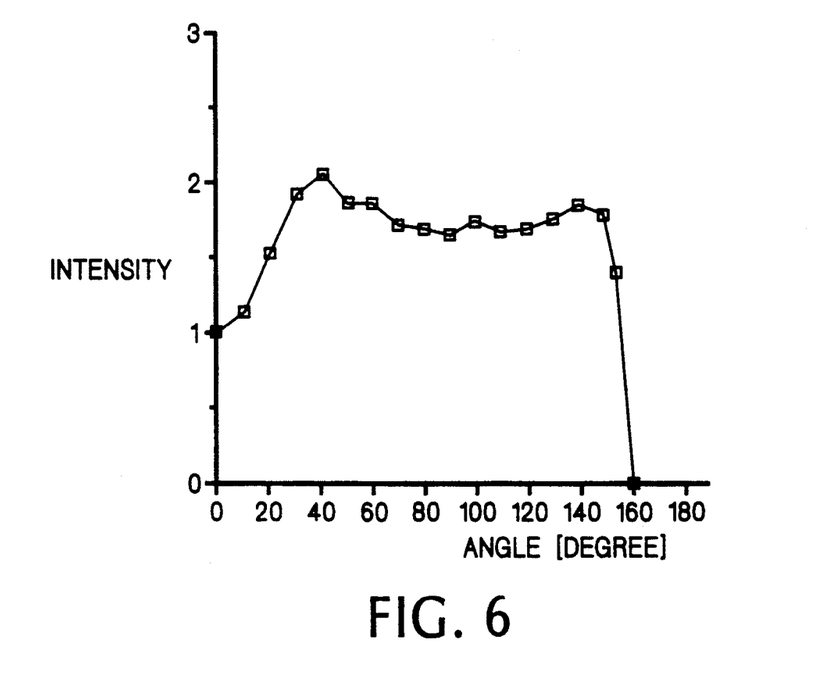
FIG. 6 is a graph which illustrates the signal intensity as a function of the angle of incident radiance for a 3 mm fluorescent fiber probe with 10% absorption, 8.8 mm fluorescent tip length, 7 mm spacer element length, and a domed proximal end.
Figure 7:
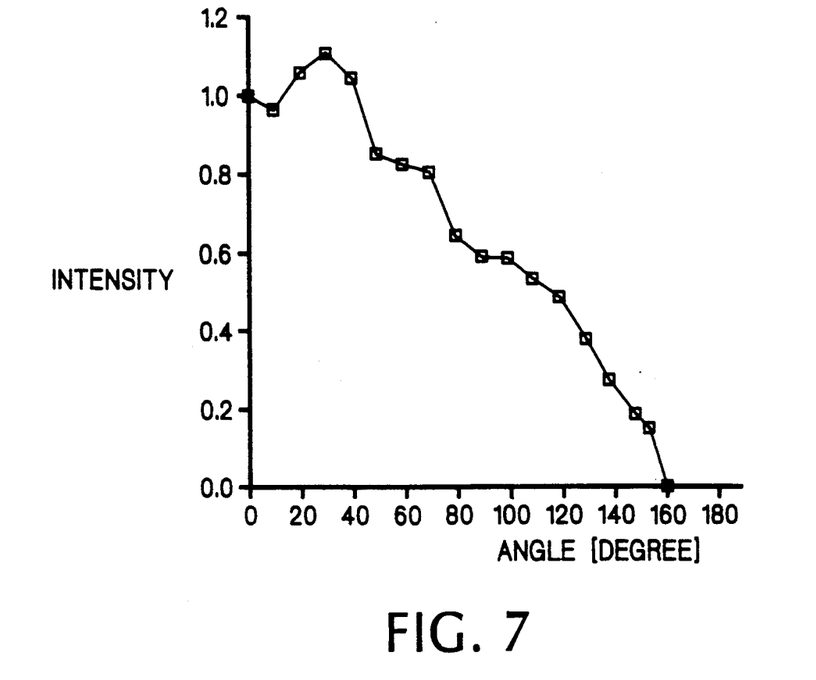
FIG. 7 is a graph which illustrates the signal intensity as a function of the angle of incident radiance for a 3 mm fluorescent fiber probe with 10% absorption, 3.3 mm fluorescent tip length, 3 mm spacer element length and a domed proximal end.
Figure 11A:
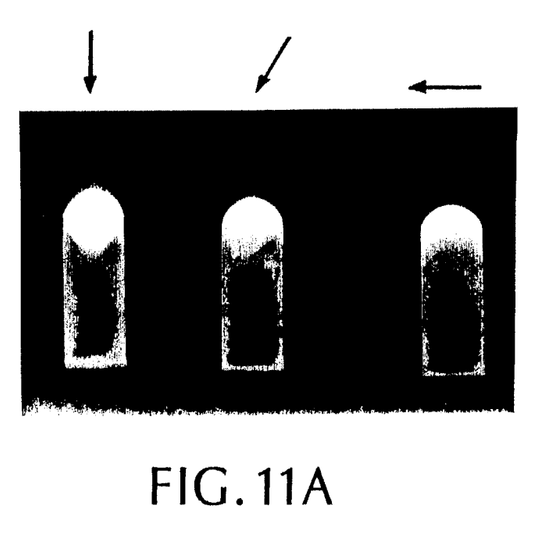
FIG. 11 is a set of photographs which illustrate the distribution of fluorescence in a 3 mm diameter fluorescence fiber probe (a, flat proximal end; b, domed proximal end) for different angles of illumination. Arrows indicate direction of the incident beam.
Figure 11B:
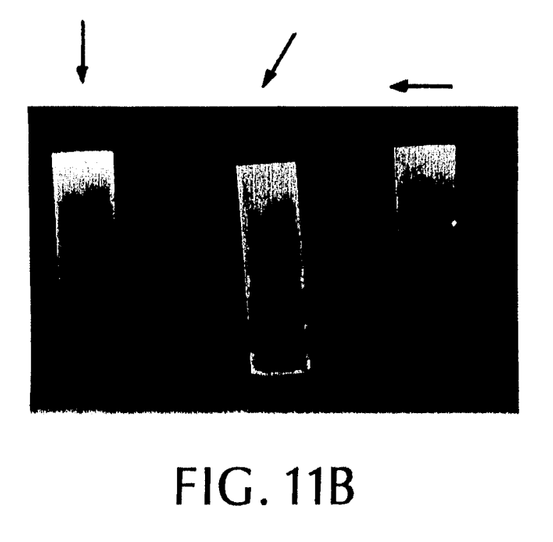

FIGS. 4–7 illustrate the dependence sensitivity (S/F) on the angle of incident radiance (S/F was normalized to 1.0 when the incident angle was 0°). For a 3 mm diameter probe the response was most isotropic under the following conditions: 10% absorption, 3 mm fluorescent tip length, 7 mm spacer element length, dome shaped proximal end (FIG. 4). The response was constant within ±10% for 0° and 150°. As seen in FIG. 11, the shape of the proximal end of the tip (e.g., domed vs flat) changes the focusing of the incident beam when irradiated from the end. This effect depends on the refractive index mismatch between the fluorescent tip and the surrounding medium and is less pronounced in tissue or liquid phantoms (see below). The effect of a flat tip is shown in FIG. 5. This shape leads to sharp inflections in the response as the angle of incident radiance is changed. With a longer fluorescent tip, as shown in FIG. 6, sensitivity is lost at small $\theta$ due to the smaller solid angle subtended by the fluorescence produced at the proximal end of the tip. This is most pronounced at high dye concentration. However, reducing the concentration results in an overall reduction in sensitivity. If the spacer element is shorter, as shown in FIG. 7, the effect is to cause shadowing of the active volume of the fiber tip bundle at larger angles and a consequent drop-off in the response.

Measurement of Signal Constancy

The constancy of the emitted fluorescence signal under high fluence rate illumination was checked by a 60 minute test illumination of a 1 $cm^2 \times 3$ cm probe rod at 0.5 $W/cm^2$. This resulted in a 7.3% increase in transmittance and 4.8% decrease in fluorescence counts from 570 nm to 615 nm as determined with a fluorescence spectrophotometer.

Influence of Surrounding Media on Performance of the Probe

Figure 8:
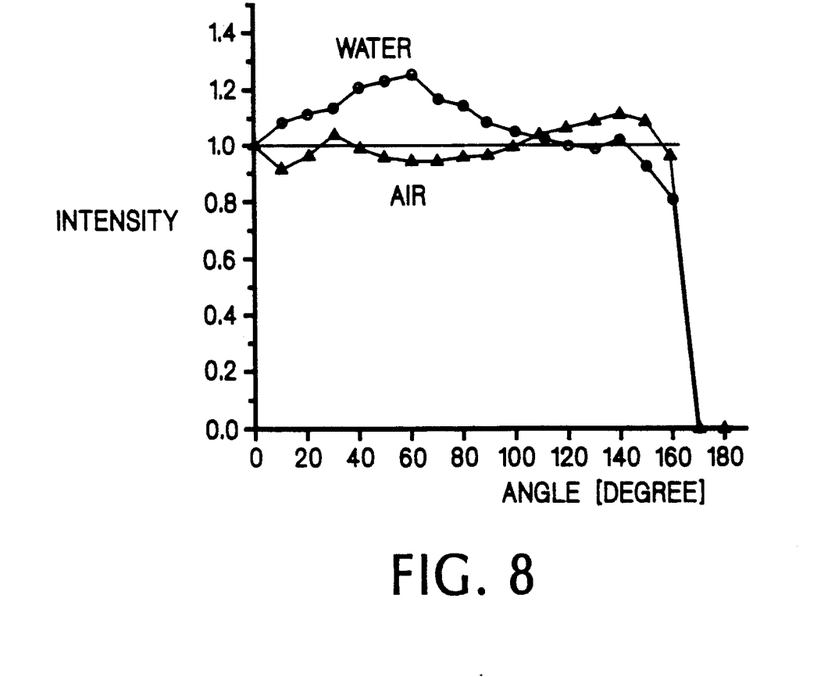
FIG. 8 is a graph which illustrates the signal intensity as a function of the angle of incident radiance for a 1.4 mm diameter fluorescent fiber probe in water (circles) and air (triangles).

As shown in FIG. 8, the refractive index of the surrounding medium slightly alters the isotropy of the fluorescent probe, up to about 20% in changing from air (n=1) to water (n=1.33). For a given refractive index, it may be possible to modify the length of the fluorescent tip and the spacer element to achieve an isotropic response within ±10%, as was done for the present probes in air. Since the refractive index of different soft tissues varies by only a few percent at the wavelengths of interest, in the approximate range of refractive indices from 1.38-1.41, a single probe will be suitable for all tissues.

The sensitivity of the probe was also found to depend on the refractive index, as has been observed for scattering tip fibers. Thus, an uncertainty in the tissue refraction index in the range 1.38-1.41 would give an uncertainty in the absolute fluence measured of about ±6%.

Evaluation in Tissue—Simulating Phantoms

Two tissue-simulating phantoms were produced, and the radiation fluence energy rate was measured vs depth with a 0.8 mm scattering ball tip (Laserguide Santa Barbara, Calif.) and a 1.4 mm diameter fluorescence fiber probe. The incident fluence was about 100 $mW/cm^2$ and the beam diameter was 50 mm.

A light scattering and absorbing liquid phantom was made by filling a 200 mm $\times$ 150 mm $\times$ 150 mm glass-walled tank with varying concentrations of Intralipid (KabiVitiam Inc., Calif.) as scatterer and India ink as absorber (Pelikan, W. Germany). This has been widely used as a phantom medium for simulating light propagation in tissues. An additional chamber in front of the tank 100 mm $\times$ 150 mm $\times$ 150 mm could be water filled to obtain refractive index matching at the surface. One side of the tank was illuminated with a 50 mm diameter argon beam. A second set of measurements were made using an 800 $\mu$m diameter scattering ball tip (Laserguide, Palo Alto, Calif.). For these measurements cut-on filter in front of the silica photodiode used for the fluorescent tip was replaced by a neutral density filter (ND Gelatin filter, Eastman Kodak, Rochester, N.Y.), the incident fluence was 100 $mW/cm^2$.

Figure 9:
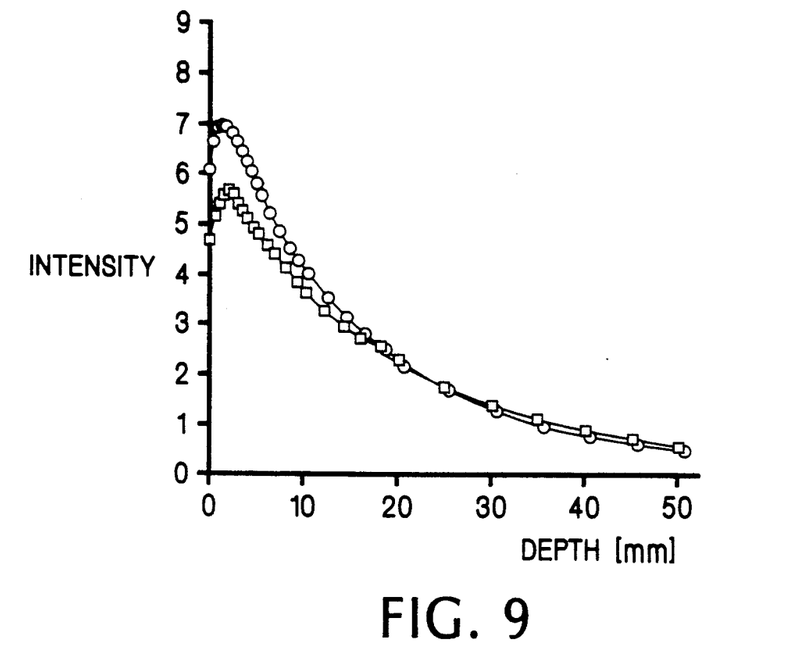
FIG. 9 is a graph which illustrates the effect of depth on signal intensity for a scattering probe (circles) and a fluorescent fiber probe (squares) for the case of matched boundary conditions.
Figure 10:
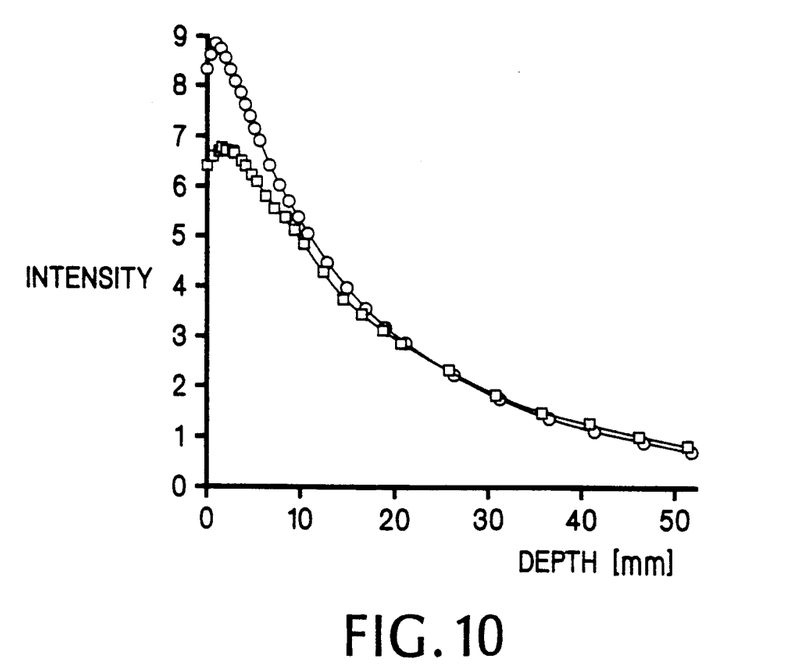
FIG. 10 is a graph which illustrates the effect of depth on signal intensity for a scattering probe (circles) and a fluorescent fiber probe (squares) for the case of unmatched boundary conditions.

In FIG. 9 the measured energy fluence rates vs depth from the front surface, corrected for the energy fluence rate measured in water, are shown. The data for the scattering ball tip were renormalized to allow comparison. Renormalisation was performed by using the intensities at depth, where the fluence profile is closest to isotropic. FIG. 9 shows the data in a scattering phantom with a 100 mm thick water layer in front of the scattering phantom simulating matched boundary conditions (a) and the same measurements with a 3 mm glass window in front of the fluorescent tip probe, simulating a non-matched boundary condition (b).

EXAMPLE 2

Fluorescent Fiber Probes with Diameters Less than 1.0 mm

Probes with diameters between between 600$\mu$ and 250$\mu$ were produced by treating an optical fiber with two solutions as follows. The first solution was prepared by polymerizing methylmethacrylate (MMA) and Azobis (1 mg/4 ml MMA) at 60° for 48 hr to generate polymethyl-methacrylate (PMMA). After complete polymerization, the PMMA was reliquified using an equal volume of dimethylchloride (DMC) to generate a PMMA-DMC solution. The second solution (PMMA-dye DMC) was prepared in an identical manner except that an appropriate fluorescent dye (see below) was dissolved in the dimethylchloride. To prepare the probe, the buffer and cladding of the optical fiber were stripped, and the core of the optical fiber was cleaved about 2 to 5 mm from the end of the buffer. The stripped fiber is submerged about 1 cm into PMMA-DMC solution so that the exposed core and a portion of the buffer will be coated. This solution partially dissolves the buffer, ensuring binding of the probe being created to the optical fiber. The fiber was withdrawn and allowed to dry so that all of the DMC evaporates. This procedure was repeated until a cylindrical spacer element of the desired length was built up extending from the end of the optical fiber. The very end of the newly created spacer element was next dipped repeatedly into the PMMA-dye DMC solution until a fluorescent tip of the desired length was built up extending from the end of the spacer element. The probe was then shaped by modeling on a small lathe using a silicon-carbide stone. Finally, the probe was cured at 60° for 12 hr. and polished with silica suspended in water.

Figure 12A:
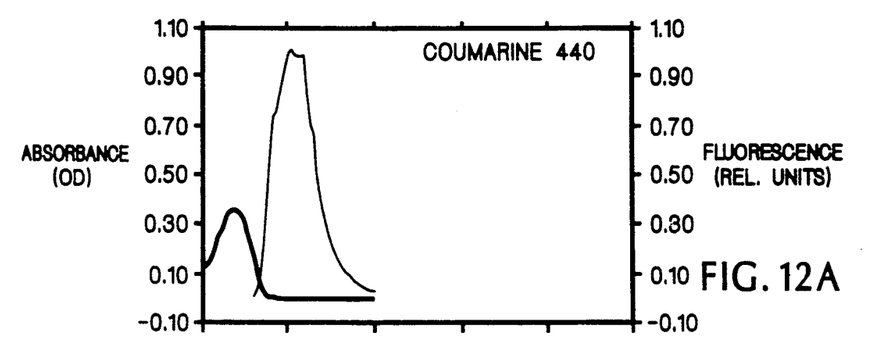
FIG. 12 is a set of three graphs which illustrate the absorption (heavy line) and emission (thin line) spectra for: coumarine 440 (a), rhodamine 610 (b), and nile blue A (c).
Figure 12B:
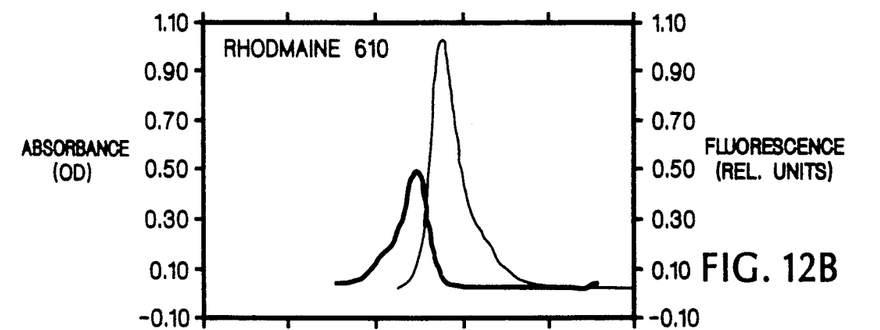
Figure 12C:
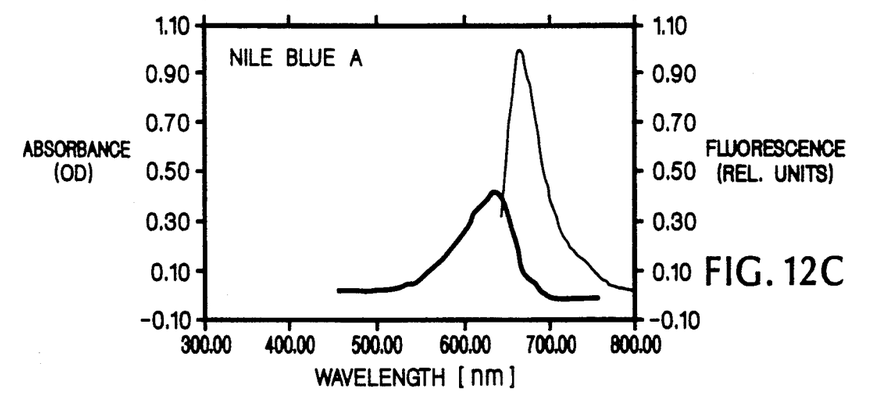

Fluorescent fiber probes smaller than 250$\mu$ were produced by diffusion of the dye into a PMMA fiber core. To create such a probe the chlorinated PMMA buffer of an optical fiber was stripped with 50° dimethyl sulfoxide. The core was then submerged in a solution of dimethylchloride saturated with dye for 60 to 180 s. The optimum time for must be empirically determined, and care must be taken so as to not dissolve the core. The dyes used were coumarine 440 (Exciton, Dayton, Ohio), Rhodamine 610 Perchlorate (Exciton, Dayton, Ohio) and Nile Blue A (Aldrich, Milwaukee, Wis.). FIG. 12 illustrates the absorption (heavy line) and emission (thin line) spectra for these three dyes. For these spectra dilute solutions (1:300 for absorbance; 1:3000 for emission) were made rom saturated dye solutions in DMC. The excitation wavelengths were 351 nm (coumarine 440), 514 nm (rhodamine 610), and 630 nm (nile blue A).

Sensitivity

The sensitivity of these fluorescent fiber probes was tested using an argon laser (Coherent, Palo Alto, Calif.) mechanically chopped at 90 Hz. The emitted fluorescence, selected by an appropriate cut-on filter, was detected by a photodiode and quantified by a look in amplifier (Stanford Research, Palo Alto, Calif.). The cut-on filter is chosen so that it allows transmission of radiance in the wavelength range emitted by the dye within the tip and blocks transmission of the excitation radiance. The sensitivity of the optical probe (S/F) was determined for several fluorescent fiber probes (Table 2). The incident fluence on the probes was measured using a power meter (Coherent, Palo Alto, Calif.) with a 19 mm diameter detector which was completely illuminated. Theoretical values for S/F were determined as described above.

TABLE 2

Comparison of Calculated and Measured Sensitivity Values

| Dye | Fiber Material | Fiber Radius (mm) | Tip Radius (mm) | S/F measured | S/F Theory |
|---|---|---|---|---|---|
| Nile Blue A | poly-imide | 0.16 | 0.2 | $2.40 \times 10^{-5}$ | $1.38 \times 10^{-5}$ |
|  | poly-imide | 0.16 | 0.19 | $1.20 \times 10^{-5}$ | $1.38 \times 10^{-5}$ |
|  | poly-imide | 0.1 | 0.15 | $1.60 \times 10^{-6}$ | $5.39 \times 10^{-6}$ |
| Rhodamine 610 | glass | 0.25 | 0.29 | $5.50 \times 10^{-5}$ | $6.74 \times 10^{-5}$ |
|  | poly-imide | 0.16 | 0.26 | $3.50 \times 10^{-5}$ | $2.76 \times 10^{-5}$ |
|  | poly-imide | 0.16 | 0.29 | $1.20 \times 10^{-5}$ | $2.76 \times 10^{-6}$ |
| Coumarine 440 | PMMA | 0.125 | 0.125 | $2.22 \times 10^{-4}$ | $3.79 \times 10^{-4}$ |

Linearity

Figure 13:
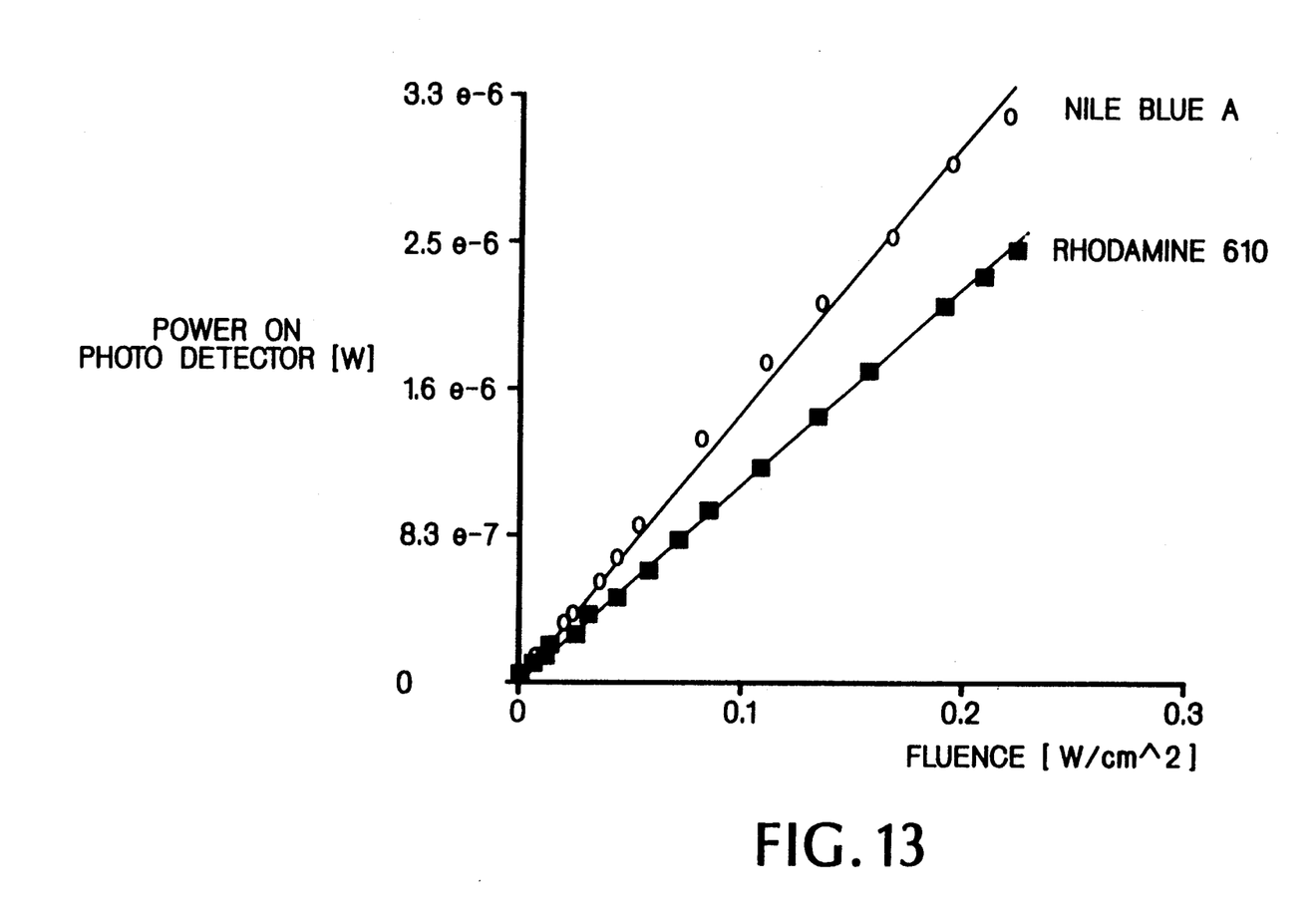
FIG. 13 is a graph which illustrates the effect of radiance fluence on signal for a fluorescent fiber probe containing nile blue A (open circles) and a fluorescent fiber probe containing rhodamine 610 (filled squares).

The linearity of probe response was tested with incident light at a 90° angle. The irradiance of the incident light was measured with a power meter (Coherent, Palo Alto, Calif.). The linearity of response for two probes is shown in FIG. 13. One is a 420 μm diameter probe with rhodamine 610 dye, submerged in water, 514 nm incident light (filled squares); the other is an 250 μm diameter probe, Coumarine 440 dye, in air, 350 nm incident light (open circles).

Isotropy

Figure 14A:
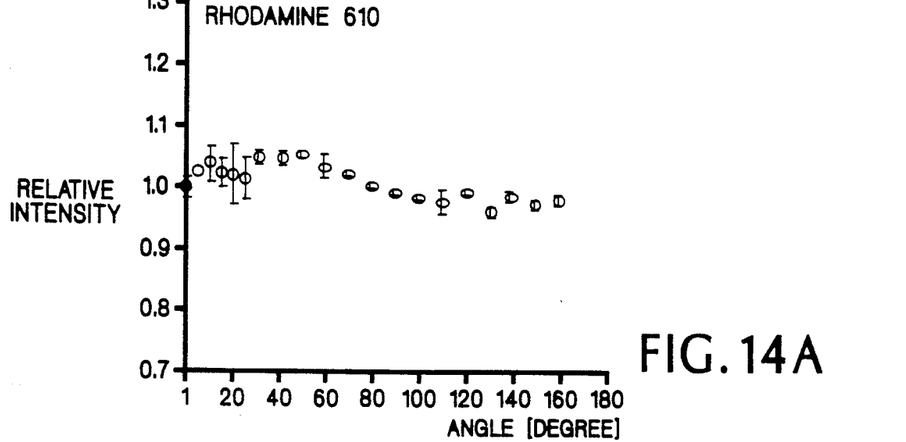
FIG. 14 is a set of three graphs which depict the effect of the angle of the incident radiance on the signal for a fluorescent fiber probe containing rhodamine 610 (a), a fluorescent probe containing nile blue A (b), and a fluorescent fiber probe containing coumarine 440 (c).
Figure 14B:
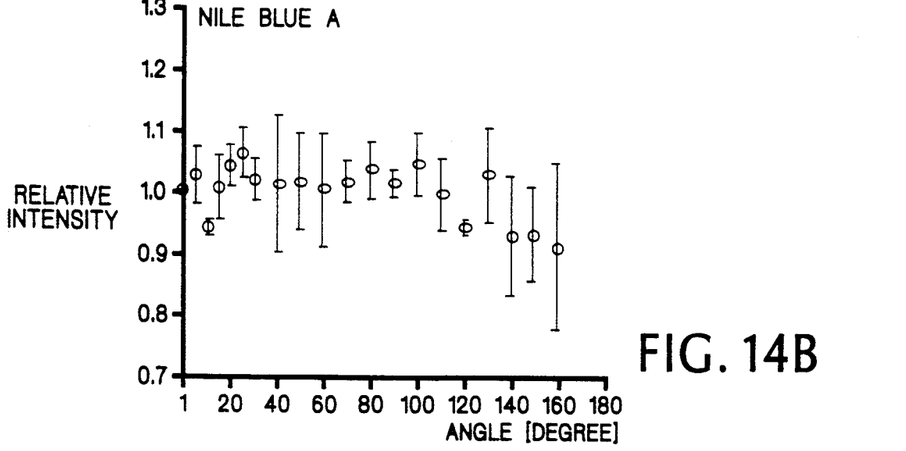
Figure 14C:
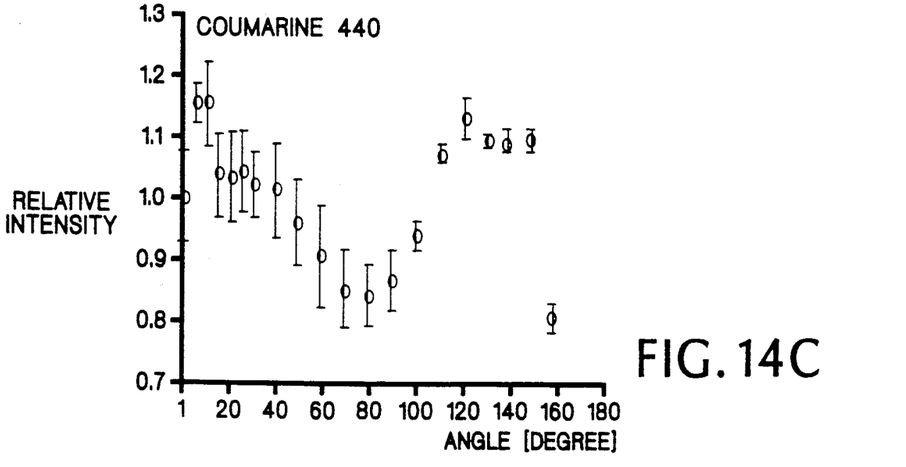

The isotropic response of the probes was measured with the probe submerged in water using green or red excitation light and with the probe in air for ultraviolet A excitation light. FIG. 14 illustrates the results of angular sensitivity measurements for a 400 μm diameter probe incorporating Nile Blue A dye fused to a 320 μm polyimide fiber (a); a 350 μm diameter probe incorporating rhodamine 610 dye fused to a 250 μm polyimide fiber (b); and a 250 μm diameter probe incorporating coumarine 440 dye fused to a 250 μm PMMA fiber (c). The smallest probe had the least isotropic response; however, with improved production techniques the response may improve.

Lifetime

Figure 15:
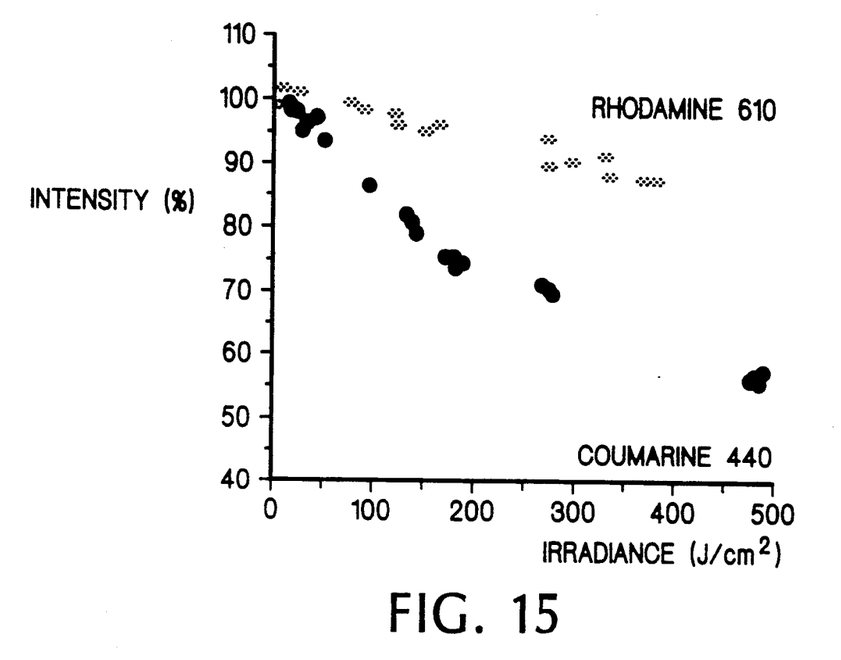
FIG. 15 is a graph which illustrates the effect of cumulative irradiance on fluorescent fiber probe response for a 400μ diameter fluorescent fiber probe incorporating rhodamine 610 dye (stippled circles) and a 200μ diameter fluorescent fiber probe incorporating coumarine 440 dye (filled circles).

The dyes used undergo photodegradation; accordingly, the photophysical history of each probe influences its performance. FIG. 15 illustrates the effect of cumulative irradiance on probe response for a 400μ diameter probe incorporating rhodamine 610 dye (stippled circles) and a 200μ diameter probe incorporating coumarine 440 dye (filled circles).

Photodegradation can also affect isotropy. For a 50μ diameter probe incorporating coumarine 440 dye, irradiated with 200 J/cm², the variation in isotropy increased from 20% prior to irradiation to 30% after irradiation. This variation was not observed for larger probes.

Prior irradiation did not affect the linearity of the response of either a 250 μm diameter probe incorporating coumarine 440 dye or a 200μ probe incorporating rhodamine 610 dye.

Sensitivity as a Function of Refractive Index

Figure 16:
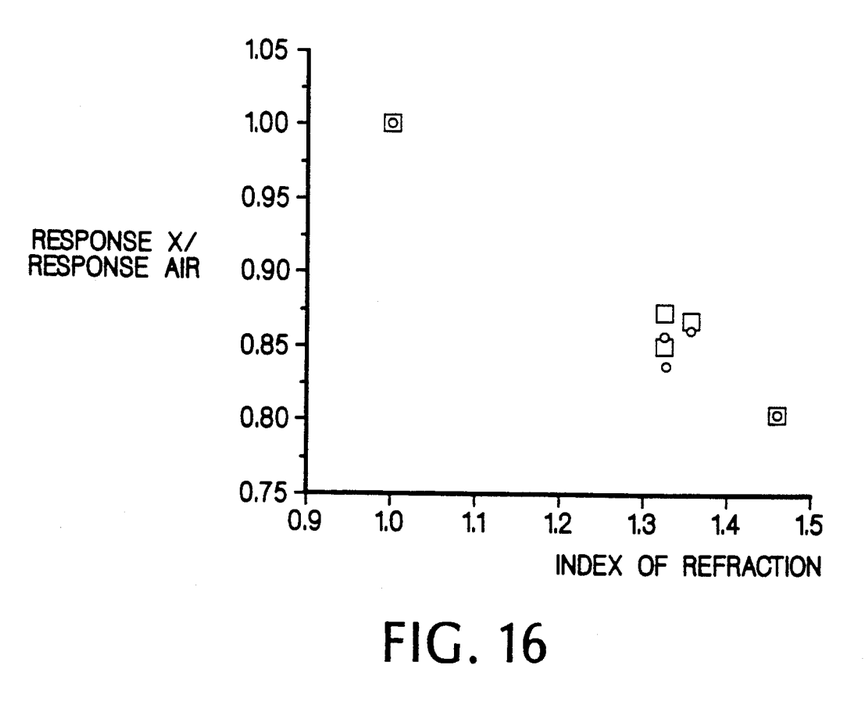
FIG. 16 is a graph which illustrates the effect of the refractive index of the media on the response of a 275μ diameter rhodamine 610 fluorescent fiber probe (open circles) and a 310μ diameter rhodamine 610 fluorescent fiber probe fused to a 200μ polyimide fiber (open squares).

The sensitivity of the probe depends on the refractive index. FIG. 16 illustrates the sensitivity (response in medium x/response in air) of two probes as a function of the refractive index of the medium. The probes were a 275 μm diameter rhodamine 610 probe fused to a 200 μm polyimide fiber (open circles) and a 310 μm diameter rhodamine 610 probe fused to a 200 μm polyimide fiber (open squares). The angle of the incident light was 90°.

USE

The probes of the inventions are used to measure radiant energy fluence in a medium (e.g., a scattering medium such as a tissue). The probe is inserted into a tissue (e.g., a tumor) and used to measure radiant energy fluence in such techniques as photodynamic therapy. The fluorescence emitted by a probe of the invention can be quantified using instrumentation similar to that presently used for other probes designed for monitoring radiant energy fluence (e.g., scattering ball probes).

We claim:

1. A probe for radiance dosimetry, said probe comprising:
   an optical fiber;
   a translucent, substantially dye-free spacer element mounted at a distal end of said fiber; and
   a tip portion disposed at a distal end of said spacer element, said tip portion containing a fluorescent dye.

2. The probe of claim 1 wherein said optical fiber and spacer element are comprised of polymethylmethacrylate.

3. The probe of claim 1 wherein said dye is Nile Blue A.

4. The probe of claim 1 wherein said dye is Rhodamine 610.

5. The probe of claim 1 wherein said dye is Coumarine 440.

6. The probe of claim 1, wherein said spacer has a diameter of less than 1 mm.

7. The probe of claim 1 wherein the diameters of said tip and said spacer are substantially equal to the diameter of said optical fiber.

8. An instrument for radiance dosimetry, said instrument comprising:

a photodiode;

an optical fiber, operably attached to said photodiode;

a translucent, substantially dye-free, spacer element mounted at a distal end of said fiber; and a tip portion disposed at a distal end of said spacer element.

9. The instrument of claim 8 wherein the diameters of said tip and said spacer are substantially equal to the diameter of said optical fiber.

* * * * *

UNITED STATES PATENT AND TRADEMARK OFFICE
CERTIFICATE OF CORRECTION

PATENT NO.   : 5,275,160

DATED        : January 4, 1994

INVENTOR(S)  : Lothar Lilge, Brian C. Wilson, and Thomas Haw

It is certified that error appears in the above-identified patent and that said Letters Patent is hereby corrected as shown below:

Column 2, line 37, replace "for radiance dosimetry the..." to --for radiance dosimetry. The...--;

Column 4, line 39, replace "The value of can be determined..." to --The value of $\alpha$ can be determined...--;

Column 7, line 14, replace $\theta$ with --$\vartheta$--;

Column 10, line 12, replace "50 $\mu$" with --250 $\mu$m--.

Signed and Sealed this

Thirty-first Day of May, 1994

Attest:

BRUCE LEHMAN

Attesting Officer     Commissioner of Patents and Trademarks